United States Patent

Bothe Almquist et al.

Patent Number: 5,445,742
Date of Patent: Aug. 29, 1995

[54] PROCESS FOR PURIFYING HALOSILANES

[75] Inventors: Catherine L. Bothe Almquist, West Chester, Ohio; Michael A. Diaz, Louisville, Ky.; Roland L. Halm, Midland, Mich.; James R. Hasler, Jr., Madison, Ind.; James S. Smith, Midland, Mich.

[73] Assignee: Dow Corning Corporation, Midland, Mich.

[21] Appl. No.: 247,812

[22] Filed: May 23, 1994

[51] Int. Cl.6 .............................. C02F 1/42; B01J 8/02
[52] U.S. Cl. ................................ 210/670; 210/690; 95/143
[58] Field of Search ..................... 92/143–147; 210/670, 690

[56] References Cited

U.S. PATENT DOCUMENTS

| 2,380,995 | 8/1945 | Rochow . | |
| 3,732,326 | 5/1973 | Chen | 95/143 X |
| 4,056,369 | 11/1977 | Quackenbush | 55/74 X |
| 4,066,423 | 1/1978 | McGill et al. | 55/58 X |
| 4,305,734 | 12/1981 | McGill | 55/25 |
| 4,338,101 | 7/1982 | Tuttle | 55/180 X |
| 4,421,532 | 12/1983 | Sacchetti et al. | 55/28 |
| 4,462,811 | 7/1984 | Dinsmore et al. | 55/18 |
| 4,554,141 | 11/1985 | Scull et al. | 95/144 |
| 4,784,672 | 11/1988 | Sircar | 55/26 |
| 5,051,117 | 9/1991 | Prigge et al. | 95/143 X |
| 5,118,329 | 6/1992 | Kosaka et al. | 95/146 X |
| 5,256,300 | 10/1993 | Cockett et al. | 210/690 X |
| 5,290,342 | 3/1994 | Wikman et al. | 95/143 |

FOREIGN PATENT DOCUMENTS

| 89396 | 4/1959 | Czech Rep. . | |
| WO84/04913 | 12/1984 | WIPO | 95/143 |

*Primary Examiner*—Robert Spitzer
*Attorney, Agent, or Firm*—William F. Boley

[57] ABSTRACT

A process for purifying halosilanes consisting of contacting a mixture comprising a halosilane and a hydrocarbon with an adsorbent selective for the hydrocarbon, thereby reducing the hydrocarbon content of the mixture. The present process is particularly useful for removing hydrocarbon contaminates from chlorosilanes, where the hydrocarbon contaminates have a boiling point similar to that of the chlorosilanes.

15 Claims, No Drawings

PROCESS FOR PURIFYING HALOSILANES

BACKGROUND OF INVENTION

The present invention is a process for the purification of halosilanes. The process consists of contacting a mixture comprising a halosilane and a hydrocarbon with an adsorbent selective for the hydrocarbon, thereby reducing the hydrocarbon content of the mixture. The present process is particularly useful for removing hydrocarbon contaminates from chlorosilanes, where the hydrocarbon contaminates have a boiling point similar to that of the chlorosilanes.

Hydrocarbon contaminates in halosilanes can create quality problems such as undesirable odor and color not only in the halosilanes, but in products made from the halosilanes. In addition, in cyclic processes using halosilanes as feed, where unreacted materials are being recovered and fed back to the process, hydrocarbons can build up in the process leading to a decrease in process capacity and operational control. Often it is hard to remove these hydrocarbon contaminates from the halosilanes by standard processes such as distillation because of similar boiling points.

The present process is particularly useful for removing hydrocarbon contaminates from halosilanes prepared by the reaction of an organohalide with silicon metalloid in the presence of a suitable catalyst, as was originally described by Rochow, U.S. Pat. No. 2,380,995, issued Aug. 7, 1945.

The use of adsorbents to recover hydrocarbons from air and hydrocarbon mixtures generated during the production and transfer of petroleum products is described, for example, in Quackenbush, U.S. Pat. No. 4,056,369, issued Nov. 1, 1977; McGill et al., U.S. Pat. No. 4,066,423, issued Jan. 3, 1978; Dinsmore et al., U.S. Pat. No. 4,462,811, issued Jul. 31, 1984; and Tuttle, U.S. Pat. No. 4,338,101, issued Jul. 6, 1982. A typical adsorbent used to recover the hydrocarbons is activated carbon.

McGill, U.S. Pat. No. 4,305,734, issued Dec. 15, 1981, describes a process for recovering methane vented from industrial operations such as coal mines. The described process consists of passing a hydrocarbon-carrier gas mixture through an adsorbent bed capable of selectively adsorbing the hydrocarbon components from the mixture to produce a stream of substantially hydrocarbon-free carrier gas. McGill teaches the process is particularly useful for separating methane from air and for separating ethylene from air or nitrogen streams which vent from polyethylene manufacturing facilities. McGill teaches activated carbon as a typical adsorbent.

Sircar, U.S. Pat. No. 4,784,6712, issued Nov. 15, 1988, teaches that activated carbon can be used to remove hydrocarbons and halohydrocarbons from methane and carbon dioxide present in landfill gases.

Sacchetti et al., U.S. Pat. No. 4,421,532, issued Dec. 20, 1983, describes a process for recovering volatile organic substances from industrial waste gases. The process involves the passing of the waste gas through a bed of an adsorbent such as activated carbon, silica gel, alumina, or molecular sieve to remove volatile organic substances, and then regenerating the adsorbent bed by stripping with steam or a hot gas.

Zizka et al., Czech. Patent No. 89396, published Apr. 15, 1959, describes a process for the recovery of methyl chloride from the direct process for producing organochlorosilanes. In the process described by Zizka et al., the gaseous mixture resulting from the direct process is first treated with a dilute NaOH of KOH solution to remove hydrolyzable methylchlorosilanes. The treated gas is then contacted with activated carbon which adsorbs the methyl chloride. The methyl chloride is recovered from the activated carbon by thermal desorption, in some cases with simultaneous pressure reduction.

The present inventors have found that hydrocarbon contaminates present in halosilane liquids and gases can be reduced by contacting the halosilane liquid or gas with an adsorbent selective for the hydrocarbon. The described art does not recognize that adsorbents can selectively adsorb hydrocarbon contaminates from halosilane liquids and gases.

SUMMARY OF INVENTION

The present invention is a process for purifying halosilanes. The process consists of contacting a mixture comprising a halosilane and a hydrocarbon with an adsorbent selective for the hydrocarbon, thereby reducing the hydrocarbon content of the mixture. The present process is particularly useful for removing hydrocarbon contaminates from chlorosilanes, where the hydrocarbon contaminates have a boiling point similar to that of the chlorosilanes.

DESCRIPTION OF INVENTION

The present invention is a process for reducing hydrocarbon content of halosilanes. The process comprises contacting a mixture comprising a halosilane and a hydrocarbon with an adsorbent selective for the hydrocarbon, thereby reducing the hydrocarbon content of the mixture.

Preferred halosilanes from which hydrocarbons can be adsorbed are described by formula $R_aH_bSiX_{4-a-b}$, where $a=0$ to 3, $b=0$ to 3, $a+b=0$ to 3, X is a halogen, and R is a monovalent hydrocarbon radical comprising one to 12 carbon atoms. The preferred halogen, X, is chlorine. R can be, for example, methyl, ethyl, propyl, tert-butyl, vinyl, allyl, and phenyl.

The halosilane can be, for example, trimethylchlorosilane, dimethyldichlorosilane, dimethylchlorosilane, phenylmethyldichlorosilane, phenyltrichlorosilane, trichlorosilane, tetrachlorosilane, methylvinyldichlorosilane, and dimethyldivinylchlorosilane.

Hydrocarbons which can be removed by the present process are those which are typically found in trace amounts in halosilanes after distillation processes. The specific types of hydrocarbons present in the halosilanes will depend upon the particular halosilane and its separation history. The hydrocarbons can include saturated hydrocarbons, unsaturated hydrocarbons, and halogenated hydrocarbons. The present process is especially useful for removing those hydrocarbons having boiling points similar to the halosilane of interest, where the hydrocarbons cannot readily be separated by distillation. The present process is especially useful for removing hydrocarbons comprising about one to 12 carbon atoms from chlorosilanes.

The mixture comprising a halosilane and a hydrocarbon is contacted with an adsorbent selective for the hydrocarbon, thereby reducing the hydrocarbon content of the mixture. The adsorbents selective for the hydrocarbon are generally characterized by the following properties (1) hydrophobic, (2) organophilic, (3) neutral surface, and (4) no polarizable pendant groups.

Examples of such adsorbents include activated carbons, high silica zeolites such as ZSM-5, and synthetic carbonaceous materials including carbon molecular sieves. Specific examples of such adsorbents are provided in the examples herein.

The mixture comprising a halosilane and a hydrocarbon can be contacted with the adsorbent selective for the hydrocarbon by standard methods for contacting a gas or liquid halosilane with a solid. Preferred is when the mixture comprising a halosilane and a hydrocarbon is a liquid. The process can be run as a batch process or as a continuous process. In a preferred process once the adsorbent becomes saturated with hydrocarbon and breakthrough occurs, the adsorbent is desorbed and reused in the process. The process can be run as a continuous process using multiple beds of adsorbent material, where adsorption and desorption of the beds is staged to provide a continuous process. Adsorption and desorption of the adsorbent selective for the hydrocarbon can be accomplished by standard methods such as a pressure swing adsorption and desorption process, a temperature swing adsorption and desorption process, or a combination of pressure and temperature swing adsorption and desorption processes. The method of desorption of the adsorbent is not critical to the present process and can be any of those methods known in the art for desorbing adsorbents.

The length of time the mixture containing halosilane and hydrocarbon is in contact with the adsorbent selective for the hydrocarbon will depend upon the particular adsorbent used, the hydrocarbon to be adsorbed, and the concentration of hydrocarbon. Examples of useful contact times are provided in the examples herein. Generally, any contact time sufficient for any or all of the hydrocarbon to be adsorbed from the mixture is considered useful.

The following examples are provided to illustrate the present invention. These examples are not intended to limit the scope of the present claims. The chlorosilanes treated in the examples were purified by distillation prior to treatment. The concentration of hydrocarbons in the chlorosilanes were determined by gas chromatography (GC) analysis using a flame ionization detector (FID).

EXAMPLE 1

(Not within scope of present invention) The ability of a crosslinked polystyrene type polymer to remove hydrocarbons from trimethylchlorosilane was evaluated. The evaluation was conducted by placing 1 g of Amberlite TM XAD-4 Resin, Rohm and Haas, Philadelphia, Pa., into a flask. A 20 g sample of trimethylchlorosilane containing 3977 ppm saturated hydrocarbons was placed in the flask. The flask containing the mixture was shaken for two hours and then a sample taken and analyzed by GC-FID. No significant reduction in the hydrocarbons content of the trimethylchlorosilane was observed.

EXAMPLE 2

(Not within scope of present invention) The ability of an ion exchange resin to remove hydrocarbons from dimethyldichlorosilane was evaluated. The evaluation was conducted by placing 5 g of XUS-40285 Ion Exchange Resin, The Dow Chemical Company, Midland, Mich., into a flask. A 42 g sample of dimethyldichlorosilane containing 410 ppm saturated hydrocarbons was placed in the flask. The flask containing the mixture was shaken for four hours and then a sample taken and analyzed by GC-FID. No significant reduction in the hydrocarbons content of the dimethyldichlorosilane was observed.

EXAMPLE 3

The ability of a high silica zeolite to remove hydrocarbons from trimethylchlorosilane was evaluated in a shaker test. The evaluation was conducted by placing 3 g of dried Purasieve TM 423 zeolite, UOP, Tarrytown, N.Y., into a flask. Purasieve 423 zeolite is described by its manufacturer as a high silica zeolite having uniform sized cavities connected by a matrix of 0.5 to 0.8 nm pores providing over 0.3 $cm^3/g$ of micropores. A 30 g sample of trimethylchlorosilane containing 2389 ppm saturated hydrocarbons, 212 ppm unsaturated hydrocarbons and 12 ppm chlorinated hydrocarbons, was added to the zeolite. The flask containing the mixture was periodically shaken for a period of 55 hours. A sample was then withdrawn from the flask and analyzed by GC-FID. The saturated hydrocarbon content of the chlorosilane sample was reduced by 94.2 percent, the unsaturated hydrocarbon content was reduced by 99.6 percent, and the chlorinated hydrocarbon content was reduced by 50 percent.

EXAMPLE 4

The ability of a high silica zeolite to remove hydrocarbons from trimethylchlorosilane was evaluated using a packed column of the zeolite. A 4.6 cm inside diameter column was loaded with 116 g of Purasieve 423 zeolite. Trimethylchlorosilane containing hydrocarbons was fed through the column at a rate of about 35 mL/h. The trimethylchlorosilane feed contained 2851 ppm saturated hydrocarbons, 21 ppm unsaturated hydrocarbons, and 67 ppm chlorinated hydrocarbons. After the adsorbent was saturated, the column was drained and the adsorbent regenerated by blowing heated nitrogen through it at a rate of 330 mL/min thereby raising the temperature of the column to 240° C. Desorbed material was collected in a cold trap at −20° C. About 3.6 g of hydrocarbons were collected in the cold trap. Trimethylchlorosilane at a rate of about 35 mL/h was again fed to the column until the adsorbent was saturated with hydrocarbons and the column desorbed as previously described. About 4.4 g of hydrocarbons were collected in the cold trap. In the trimethylchlorosilane collected from the column, the saturated hydrocarbons content was reduced by 96.8 percent, the unsaturated hydrocarbons content was reduced by 95.2 percent, and no chlorinated hydrocarbons were detected.

EXAMPLE 5

The ability of a synthetic carbonaceous adsorbent to remove hydrocarbons from trimethylchlorosilane was evaluated. The evaluation was conducted by placing 0.5 g of Ambersorb TM 575 carbonaceous adsorbent, Rohm and Haas, Philadelphia, Pa., into a flask. Ambersorb 575 is reported by its manufacturer to be a pyrolyzed sulfonated styrene/divinylbenzene resin having a mesoporosity of 0.20 mL/g and a surface area of 800 $m^2/g$. A 10 g sample of trimethylchlorosilane containing 3696 ppm of saturated hydrocarbons, 17 ppm of unsaturated hydrocarbons, and 25 ppm of chlorinated hydrocarbons was added to the flask. The flask was shaken for two hours then a sample was taken from the flask and analyzed by GC-FID. Analysis of the chlorosilane sample showed that the saturated hydrocarbon content was reduced by 22.7 percent, the unsaturated hydrocarbons content was reduced by 52.9 percent, and the chlorinated hydrocarbons content was reduced by 44.0 percent.

EXAMPLE 6

The ability of a high silica zeolite to remove hydrocarbons from dimethyldichlorosilane was evaluated. The evaluation was conducted by placing 5 g of dried Purasieve 423 zeolite into a flask. A 42 g sample of dimethyldichlorosilane containing 410 ppm unsaturated hydrocarbons was added to the flask. The flask was shaken for four hours and then a sample was taken from the flask and analyzed by GC-FID. The unsaturated hydrocarbons content of the chlorosilane sample was reduced by 44.2 percent.

EXAMPLE 7

The ability of a synthetic carbonaceous adsorbent to remove hydrocarbons from dimethyldichlorosilane was evaluated. The evaluation was conducted by placing 5 g of Ambersorb 575 carbonaceous adsorbent and 42 g of dimethyldichlorosilane as described in Example 6 into a flask. The flask was shaken for four hours and then a sample was taken from the flask and analyzed by GC-FID. The unsaturated hydrocarbons content of the chlorosilane sample was reduced by 60 percent.

EXAMPLE 8

The ability of an activated carbon to remove hydrocarbons from dimethyldichlorosilane was evaluated. The evaluation was conducted by placing 5 g of PWA Pulverized Activated Carbon, Calgon, Pittsburgh, Pa., into a flask. A 42 g sample of dimethyldichlorosilane containing 410 ppm unsaturated hydrocarbons was added to the flask. The flask was shaken for four hours and then a sample was taken from the flask and analyzed by GC-FID. The unsaturated hydrocarbons content of the chlorosilane sample was reduced by 56.6 percent.

EXAMPLE 9

The ability of an activated carbon to remove hydrocarbons from dimethyldichlorosilane was evaluated. The evaluation was conducted by placing 5 g of 114A AWD Activated Carbon, Calgon, Pittsburgh, Pa., into a flask. A 42 g sample of dimethyldichlorosilane containing 410 ppm unsaturated hydrocarbons was added to the flask. The flask was shaken for four hours and then a sample was taken from the flask and analyzed by GC-FID. The unsaturated hydrocarbons content of the chlorosilane sample was reduced by 54.4 percent.

EXAMPLE 10

The ability of a synthetic carbonaceous adsorbent to remove hydrocarbons from dimethylchlorosilane was evaluated. The evaluation was conducted by placing 5 g of Ambersorb 575 carbonaceous adsorbent into a flask. A 37 g sample of dimethylchlorosilane containing 791 ppm saturated hydrocarbons, 3782 ppm unsaturated hydrocarbons, and 2612 ppm chlorinated hydrocarbons was added to the flask. The flask was shaken for four hours and then a sample was taken from the flask and analyzed by GC-FID. The saturated hydrocarbons content of the chlorosilane sample was reduced by 16.3 percent, the unsaturated hydrocarbons content was reduced by 10.8 percent and the chlorinated hydrocarbons content wets reduced by 34.4 percent.

EXAMPLE 11

The ability of an activated carbon to remove hydrocarbons from dimethylchlorosilane was evaluated. The evaluation was conducted by placing 5 g of PWA Pulverized Activated Carbon and 37 g of dimethylchlorosilane as described in Example 10 into a flask. The flask was shaken for four hours and then a sample was taken from the flask and analyzed by GC-FID. The saturated hydrocarbons content of the chlorosilane sample was reduced by 7.0 percent, the unsaturated hydrocarbons content was reduced by 14.1 percent, and the chlorinated hydrocarbons content was reduced by 2.2 percent.

EXAMPLE 12

The ability of an activated carbon to remove hydrocarbons from dimethylchlorosilane was evaluated. The evaluation was conducted by placing 5 g of 114A AWD Activated Carbon and 37 g of dimethylchlorosilane as described in Example 10 into a flask. The flask was shaken for four hours and then a sample was taken from the flask and analyzed by GC-FID. The saturated hydrocarbons content of the chlorosilane sample was reduced by 21.0 percent, the unsaturated hydrocarbons content was reduced by 8.1 percent, and chlorinated hydrocarbons content was reduced by 75.6 percent.

EXAMPLE 13

The ability of a high silica zeolite to remove hydrocarbons from phenylmethyldichlorosilane was evaluated. The evaluation was conducted by placing 5 g of Purasieve 423 zeolite into a flask. A 45 g sample of phenylmethyldichlorosilane containing 940 ppm chlorinated hydrocarbons, 2979 ppm aromatic hydrocarbons, and 29 ppm chlorinated aromatic hydrocarbons was added to the flask. The flask was shaken for four hours and then a sample was taken from the flask and analyzed by GC-FID. The chlorinated hydrocarbons content of the chlorosilane sample was reduced by 98.7 percent, the aromatic hydrocarbons content was reduced by 84.4 percent, and chlorinated aromatic hydrocarbons were not detected.

EXAMPLE 14

The ability of a synthetic carbonaceous adsorbent to remove hydrocarbons from phenylmethyldichlorosilane was evaluated. The evaluation was conducted by placing 5 g of Ambersorb 575 carbonaceous adsorbent and 45 g of phenylmethyldichlorosilane as described in Example 13 into a flask. The flask was shaken for four hours and then a sample was taken from the flask and analyzed by GC-FID. The chlorinated hydrocarbons content of the chlorosilane sample was reduced by 93.7 percent, the aromatic hydrocarbons content was reduced by 99.0 percent and chlorinated aromatic hydrocarbons were not detected.

EXAMPLE 15

The ability of an activated carbon to remove hydrocarbons from phenylmethyldichlorosilane was evaluated. The evaluation was conducted by placing 5 g of PWA Pulverized Activated Carbon and 45 g of phenylmethyldichlorosilane as described in Example 14 into a flask. The flask was shaken for four hours and then a sample was taken from the flask and analyzed by GC-FID. The chlorinated hydrocarbons content of the chlorosilane sample was reduced by 28.3 percent, the aromatic hydrocarbons content was reduced by 59.4 percent, and the chlorinated hydrocarbons content was reduced by 30.4 percent.

EXAMPLE 16

The ability of an activated carbon to remove hydrocarbons from phenylmethyldichlorosilane was evaluated. The evaluation was conducted by placing 5 g of 114A AWD Activated Carbon and 45 g of phenylmethyldichlorosilane as described in Example 13 into a flask. The flask was shaken for four hours and then a sample was taken from the flask and analyzed by GC-FID. The chlorinated hydrocarbons content of the chlorosilane sample was reduced by 75.7 percent, the aromatic hydrocarbons content was reduced by 89.6 percent, and the chlorinated aromatic hydrocarbons content was reduced by 32.3 percent.

EXAMPLE 17

The ability of a high silica zeolite to remove hydrocarbons from phenyltrichlorosilane was evaluated. The evaluation was conducted by placing 3 g of Purasieve 423 zeolite into a flask. A 60 g sample of phenyltrichlorosilane containing 462 ppm of aromatic hydrocarbons was placed in the flask. The flask was shaken for four hours and then a sample was taken from the flask and analyzed by GC-FID. The aromatic hydrocarbons content of the chlorosilane sample was reduced by 88.8 percent.

EXAMPLE 18

The ability of a synthetic carbonaceous adsorbent to remove hydrocarbons from phenyltrichlorosilane was evaluated. The evaluation was conducted by placing 3 g of Ambersorb 575 carbonaceous adsorbent and 60 g of phenyltrichlorosilane as described in Example 18 into a flask. The flask was shaken for four hours and then a sample was taken from the flask and analyzed by GC-FID. The aromatic hydrocarbons content of the chlorosilane mixture was reduced by 90.2 percent.

EXAMPLE 19

The ability of a high silica zeolite to remove hydrocarbons from trichlorosilane was evaluated. The evaluation was conducted by placing 5 g of Purasieve 423 zeolite into a flask. A 42 g sample of trichlorosilane containing 847 ppm saturated hydrocarbon was added to the flask. The flask was shaken for four hours and then a sample was taken from the flask and analyzed by GC-FID. The saturated hydrocarbon content of the chlorosilane sample was reduced by 22.0 percent.

EXAMPLE 20

The ability of a high silica zeolite to remove hydrocarbons from tetrachlorosilane was evaluated. The evaluation was conducted by placing 5 g of Purasieve 423 zeolite into a flask. A 48 g sample of tetrachlorosilane containing 1216 ppm saturated hydrocarbons was added to the flask. The flask was shaken for four hours and then a sample was taken from the flask and analyzed by GC-FID. The saturated hydrocarbon content of the chlorosilane sample was reduced by 20.7 percent.

EXAMPLE 21

The ability of a synthetic carbonaceous adsorbent to remove hydrocarbons from tetrachlorosilane was evaluated. The evaluation was conducted by placing 5 g of Ambersorb 575 carbonaceous adsorbent and 48 g of tetrachlorosilane as described in Example 20 into a flask. The flask was shaken for four hours and then a sample was taken from the flask and analyzed by GC-FID. The saturated hydrocarbon content of the chlorosilane sample was reduced by 21.1 percent.

EXAMPLE 22

The ability of an activated carbon to remove hydrocarbons from tetrachlorosilane was evaluated. The evaluation was conducted by placing 5 g of PWA Pulverized Activated Carbon and 48 g of tetrachlorosilane as described in Example 20 into a flask. The flask was shaken for four hours and then a sample was taken from the flask and analyzed by GC-FID. The saturated hydrocarbon content of the chlorosilane sample was reduced by 3.1 percent.

EXAMPLE 23

The ability of an activated carbon to remove hydrocarbons from tetrachlorosilane was evaluated. The evaluation was conducted by placing 5 g of 114A AWD Activated Carbon and 48 g of tetrachlorosilane as described in Example 21 into a flask. The flask was shaken for four hours and then a sample was taken from the flask and analyzed by GC-FID. The saturated hydrocarbon content of the chlorosilane sample was reduced by 6.7 percent.

EXAMPLE 24

The ability of a high silica zeolite to remove hydrocarbons from dimethylvinylchlorosilane was evaluated. The evaluation was conducted by placing 5 g of dried Purasieve 423 zeolite into a flask. A 37 g sample of dimethylvinylchlorosilane containing 134 ppm saturated hydrocarbons, 858 ppm unsaturated hydrocarbons, and 1557 ppm chlorinated hydrocarbons was added to the flask. The flask was shaken for four hours and then a sample was taken from the flask and analyzed by GC-FID. The saturated hydrocarbons content of the chlorosilane sample was reduced by 94.8 percent, the unsaturated hydrocarbons content was reduced by 97.4 percent, and the chlorinated hydrocarbons content was reduced by 37.3 percent.

EXAMPLE 25

The ability of a synthetic carbonaceous adsorbent to remove hydrocarbons from dimethylvinylchlorosilane was evaluated. The evaluation was conducted by placing 5 g of Ambersorb 575 carbonaceous adsorbent and 36 g of dimethylvinylchlorosilane as described in Example 24 into a flask. The flask was shaken for four hours and then a sample was taken from the flask and analyzed by GC-FID. The saturated hydrocarbons content of the chlorosilane sample was reduced by 85.8 percent, the unsaturated hydrocarbons content was reduced by 98.4 percent, and the chlorinated hydrocarbons content was reduced by 37.3 percent.

EXAMPLE 26

The ability of an activated carbon to remove hydrocarbons from dimethylvinylchlorosilane was evaluated. The evaluation was conducted by placing 5 g of PWA Pulverized Activated Carbon and 35 g of dimethylvinylchlorosilane as described in Example 24 into a flask. The flask was shaken for four hours and then a sample was taken from the flask and analyzed by GC-FID. The saturated hydrocarbons content of the chlorosilane sample was reduced by 67.2 percent, the unsaturated hydrocarbons content was reduced by 90.8 percent, and chlorinated hydrocarbons content was reduced by 32.4 percent.

EXAMPLE 27

The ability of an activated carbon to remove hydrocarbons from dimethylvinylchlorosilane was evaluated. The evaluation was conducted by placing 5 g of 114A AWD Activated Carbon and 37 g of dimethylvinylchlorosilane as described in Example 24 into a flask. The flask was shaken for four hours and then a sample was taken from the flask and analyzed by GC-FID. The saturated hydrocarbons content of the chlorosilane sample was reduced by 86.6 percent, the unsaturated hydrocarbon content was reduced by 98.5 percent, and the chlorinated hydrocarbon content was reduced by 38.7 percent.

We claim:

1. A process for reducing hydrocarbon content of halosilanes, the process comprising: contacting a liquid mixture comprising a halosilane and a hydrocarbon with an adsorbent selective for the hydrocarbon, thereby reducing the hydrocarbon content of the mixture.

2. A process according to claim 1, where the halosilane is a chlorosilane described by formula $R_aH_bSiCl_{4-a-b}$, $a=0$ to 3, $b=0$ to 3, $a+b=0$ to 3, and each R is a monovalent hydrocarbon radical comprising one to 12 carbon atoms.

3. A process according to claim 2, where each R is independently selected from a group consisting of methyl, vinyl, and phenyl.

4. A process according to claim 1, where the process is run as a continuous process using multiple beds of adsorbent material and adsorption and desorption of the beds is staged to provide a continuous process.

5. A process according to claim 1, where the adsorbent is selected from a group consisting of activated carbons, synthetic carbonaceous materials, and high silica zeolites.

6. A process according the claim 1, where the adsorbent is a high silica zeolite, the hydrocarbon comprises about one to 12 carbon atoms, and the halosilane is selected from a group consisting of trimethylchlorosilane, dimethyldichlorosilane, phenylmethyldichlorosilane, phenyltrichlorosilane, trichlorosilane, tetrachlorosilane, and dimethylvinylchlorosilane.

7. A process according to claim 1, where the adsorbent is activated carbon, the hydrocarbon comprises about one to 12 carbon atoms, and the halosilane is selected from a group consisting of dimethyldichlorosilane, dimethylchlorosilane, phenylmethyldichlorosilane, tetrachlorosilane, and dimethylvinylchlorosilane.

8. A process according to claim 1, where the adsorbent is a synthetic carbonaceous material, the hydrocarbon comprises about one to 12 carbon atoms, and the halosilane is selected from a group consisting of trimethylchlorosilane, dimethyldichlorosilane, dimethylchlorosilane, phenylmethyldichlorosilane, phenyltrichlorosilane, tetrachlorosilane, and dimethylvinylchlorosilane.

9. A process for reducing hydrocarbon content of chlorosilanes, the process comprising:
   (A) contacting a liquid mixture comprising a chlorosilane described by formula $R_aH_bSiCl_{4-a-b}$, where $a=0$ to 3, $b=0$ to 3, $a+b=0$ to 3, and R is a monovalent hydrocarbon radical comprising one to 12 carbon atoms, and a hydrocarbon comprising one to 12 carbon atoms with an adsorbent selective for the hydrocarbon, thereby recovering a chlorosilane reduced in hydrocarbon content,
   (B) desorbing the adsorbent to remove the hydrocarbon, and
   (C) reusing the adsorbent as described in steps (A) and (B).

10. A process according to claim 9, where desorbing the adsorbent is accomplished by reducing the pressure below that pressure at which the mixture was contacted with the adsorbent.

11. A process according to claim 9, where desorbing the adsorbent is accomplished by raising the temperature of the process higher than that at which the mixture was contacted with the adsorbent.

12. A process according to claim 9, where the adsorbent is selected from a group consisting of activated carbons, synthetic carbonaceous materials, and high silica zeolites.

13. A process according to claim 9, where the adsorbent is a high silica zeolite and the chlorosilane is selected from a group consisting of trimethylchlorosilane, dimethyldichlorosilane, phenylmethyldichlorosilane, phenyltrichlorosilane, trichlorosilane, tetrachlorosilane, and dimethylvinylchlorosilane.

14. A process according to claim 9, where the adsorbent is activated carbon and the chlorosilane is selected from a group consisting of dimethyldichlorosilane, dimethylchlorosilane, phenylmethyldichlorosilane, tetrachlorosilane, and dimethylvinylchlorosilane.

15. A process according to claim 9, where the adsorbent is a synthetic carbonaceous material and the chlorosilane is selected from a group consisting of trimethylchlorosilane, dimethyldichlorosilane, dimethylchlorosilane, phenylmethyldichlorosilane, phenyltrichlorosilane, tetrachlorosilane, and dimethylvinylchlorosilane.

* * * * *